United States Patent [19]

Koono et al.

[11] Patent Number: 4,933,447

[45] Date of Patent: Jun. 12, 1990

[54] QUINOLINE DERIVATIVES

[75] Inventors: Fujiko Koono, Narita; Norimitsu Umehara, Tokorozawa; Hideaki Matsuda, Abiko; Tatsuhiko Katori, Ibaraki, all of Japan

[73] Assignee: SS Pharmaceutical Co., Ltd., Tokyo, Japan

[21] Appl. No.: 245,224

[22] Filed: Sep. 16, 1988

[30] Foreign Application Priority Data

Sep. 24, 1987 [JP] Japan .................................. 62-239348

[51] Int. Cl.$^5$ .................. A61K 31/47; A61K 31/535; C07D 413/04; C07D 215/38
[52] U.S. Cl. ..................................... 544/128; 544/80; 544/333; 544/363; 546/167; 546/169; 546/170; 546/171
[58] Field of Search ............... 546/167, 169, 170, 171; 544/128, 363, 80, 333

[56] References Cited

U.S. PATENT DOCUMENTS

| | | | |
|---|---|---|---|
| 4,036,963 | 7/1977 | Gialdi et al. | 546/170 X |
| 4,511,393 | 4/1985 | Hagen et al. | 546/167 X |
| 4,711,890 | 12/1987 | Dubroeucq et al. | 546/169 X |
| 4,715,889 | 12/1987 | Hagen et al. | 546/169 X |
| 4,797,148 | 1/1989 | Hagen et al. | 546/169 X |
| 4,804,404 | 2/1989 | Hagen et al. | 546/170 X |

OTHER PUBLICATIONS

*Chemical Abstract*, vol. 98, No. 1, Jan. 3, 1983, Columbus, Ohio, U.S.A., Kumar, V. Vijaya et al., "Formation Constants and Thermodynamic Parameters of Iron (II) Chelates with Quinoline-8-Carboxylic and Quinoxaline-2-Carboxylic Acids and their Substituted Derivatives in Aqueous Ethanol Medium".

*Chemical Abstract*, vol. 109, No. 11, Sep. 12, 1988, Konno Fujiko et al., "Preparation of Aminoquinoline Derivatives as Antiinflammatory Agents and Cardiotonics".

*Chemical Abstract*, vol. 83, No. 23, Dec. 8, 1975, Hughes, John L. et al., "Cardiovascular Activity of Aromatic Guanidine Compounds".

*Chemical Abstract*, vol. 105, No. 13, Sep. 29, 1986, Dionne Gervais et al., "Ligand-Receptor Interactions via Hydrogen-Bond Formation, Synthesis and Pharmacological Evaluation of Pyrrolo and Pyrido Analogs of the Cardiotonic Agent 7-Hydroxycylindole".

Primary Examiner—Mary C. Lee
Assistant Examiner—Joseph McKane
Attorney, Agent, or Firm—Oblon, Spivak, McClelland, Maier & Neustadt

[57] ABSTRACT

A quinoline derivative represented by the following formula is disclosed.

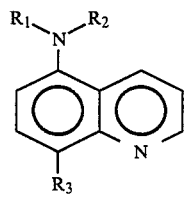

wherein $R_1$ represents a hydrogen atom or an alkyl group which may contain a substituent and $R_2$ represents an alkyl group which may contain a substituent, or $R_1$ and $R_2$ in combination with each other and with the adjacent nitrogen atom from a ring which may contain a nitrogen atom other than said adjacent nitrogen atom, an oxygen atom, or a substituent, and $R_3$ represents a cyano group, a carbamoyl group, or a lower alkoxycarbonyl group. The compound exhibits superior cardiotonic activity and vasodilative activity, and thus is effective as a medicine.

6 Claims, No Drawings

QUINOLINE DERIVATIVES

BACKGROUND OF THE INVENTION

1. Field of the Invention

This invention relates to a novel quinoline derivative, and, more particularly, to a novel quinoline derivative which is useful as a medicine.

2. Description of the Background

There are many quinoline derivatives known in the art. Among them, di-substituted quinoline derivatives having a pharmaceutical activity are quinophene having analgesic or antiphlogistic activities, dibucaine hydrochloride possessing anaesthetic activity, chloroquine phosphate, pentaquine phosphate and quinine used as an antimalarial agent, and quinidine as an antiarrhythmic agent. There has been, however, no knowledge surfaced about a pharmaceutical effect of 5,8-di-substituted quinoline derivatives.

The present inventors have synthesized various 5,8-di-substituted quinoline derivatives to study their pharmaceutical effects, and found that the novel compound represented by the following formula (I) exhibited a strong cardiotonic or vasodilative activity and was useful as a medicine for coronary disease treatment. Such a finding has led to the completion of this invention.

SUMMARY OF THE INVENTION

Accordingly, an object of the present invention is to provide a quinoline derivative represented by the following formula (I):

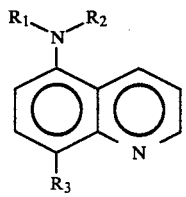

wherein $R_1$ represents a hydrogen atom or an alkyl group which may contain a substituent and $R_2$ represents an alkyl group which may contain a substituent, or $R_1$ and $R_2$ in combination with each other and with the adjacent nitrogen atom form a ring which may contain a nitrogen atom other than said adjacent nitrogen atom, an oxygen atom, or a substituent, and $R_3$ represents a cyano group, a carbamoyl group, or a lower alkoxycarbonyl group.

Other objects, features and advantages of the invention will hereinafter become more readily apparent from the following description.

DETAILED DESCRIPTION OF THE INVENTION AND PREFERRED EMBODIMENTS

Desirable alkyl groups represented by $R_1$ and $R_2$ in formula (I) are those having 1 to 12 carbon atoms. Given as substituents for these alkyl groups are, for example, hydroxyl groups, amino groups, alkylamino groups, dialkylamino groups, morpholino groups, ureido groups which may be substituted with alkyl groups, acyloxy groups, such as alkanoyloxy groups or aroyloxy groups, and the like. The alkyl groups have one or more of these substituents. Also, given as example of rings formed by $R_1$ and $R_2$ in combination are pyrrolidine, piperidine, piperazine, morpholine, pyrrole, imidazole, pyridine, pyrimidine, and the like. They may be substituted with the above-mentioned alkyl group which may have substituent groups or with the abovementioned substituent groups for the alkyl group. A typical example of a piperazine ring formed by $R_1$ and $R_2$ in combination is that represented by formula:

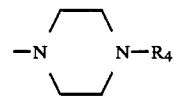

wherein $R_4$ represents an alkyl group which may have a substituent, an aralkyl group such as a phenyl alkyl group, an aryl group such as a phenyl or naphthyl group, an acyl group such as an alkanoyl, aroyl, or heteroaroyl group, a formyl group, or a carbamoyl group which may be substituted with an alkyl group.

The compound of formula (I) of this invention can be prepared, for example, according to the following processes.

Process 1

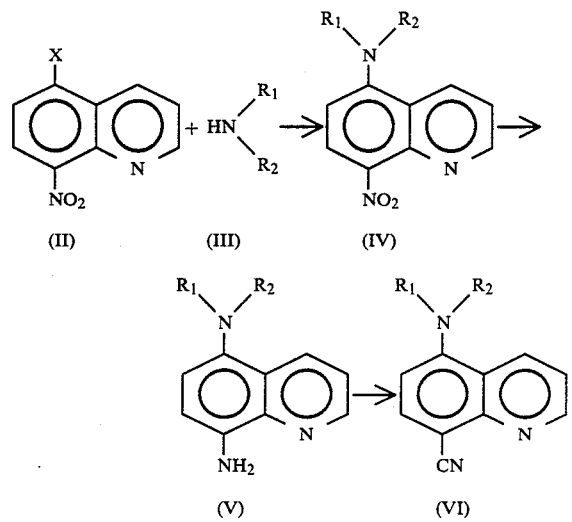

wherein X represents a halogen atom and $R_1$ and $R_2$ have the same meanings as defined above.

An amino compound (III) is reacted with 5-halogeno-8-nitroquinoline (II) to produce 5-substituted-8-nitroquinoline (IV), which is reduced into 5-substituted-8-aminoquinoline (V). The amino group of this compound is then converted into a cyano group to produce 5-substituted-8-quinolinecarbonitrile (Ia).

In these reactions, the amination is carried out by using 2 to 8 mols of the compound (III) per 1 mol of the compound (II) and by stirring the reaction mixture for 1 to 20 hours at room temperature or at a refluxing point of the solvent used. Methanol, ethanol, ethoxyethanol, methoxyethanol, dioxane, dimethylformamide, pyridine, or the like can be used as a solvent. After the reaction, the solvent is removed by evaporation, and the target compound (Ia) is obtained by extracting the residue with a solvent such as chloroform, followed by purification of the extract with silica gel column chromatography or by recrystallization.

The reduction of compound (IV) into compound (V) can be effected either catalytically or by the use of a metal and an acid. The catalytic reduction is performed in a solvent such as alcohol or the like in the presence of a catalyst and in a hydrogen atmosphere at room temperature while stirring the reaction mixture. Palladium-carbon, palladium black, platinum black, or the like is used as a catalyst. The reduction by a metal and an acid is implemented using iron, zinc, tin, stannous chloride, or the like as a metal, and hydrochloric acid or the like as an acid. The reaction is carried out at a temperature from room temperature to 100° C. for 1 to 5 hours. After completion of the reaction, the reaction mixture is neutralized with an alkali, followed by extraction with ethyl acetate or the like to obtain compound (V). The conversion of the amino group of compound (V) into cyano group is carried out by first producing a diazonium salt using sodium nitrite, isoamyl nitrite, or the like, and then by charging the diazonium salt into a cyanizing agent such as an aqueous solution of cuprous cyanide and stirring the mixture at 0° to 70° C. for several hours. The mixture is extracted with a solvent such as ethyl acetate and the extract is subjected to silica gel column chromatography or recrystallization to obtain compound (Ia) in a purified form.

Process 2

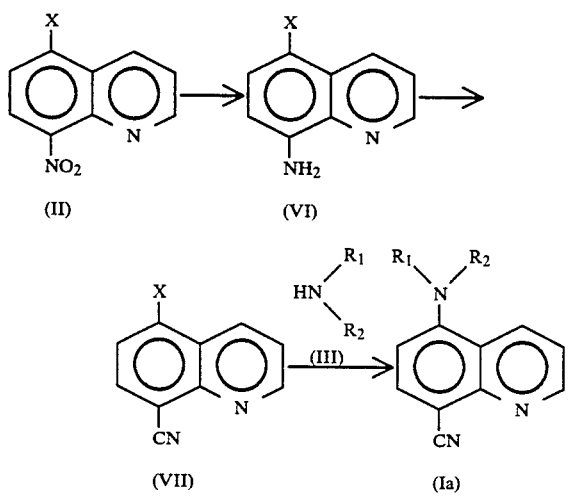

wherein X represents a halogen atom and $R_1$ and $R_2$ have the same meanings as defined above.

5-Halogeno-8-nitroquinoline (II) is reduced into 5-halogeno-8-aminoquinoline (VI), which is cyanized into compound (VII). The compound (VII) is then reacted with an amino compound (III) to produce the quinoline derivative (Ia).

The reduction is carried out using a metal and an acid. Iron, zinc, tin, stannous chloride, or the like is used as a metal, and hydrochloric acid or the like is used as an acid. The reaction is carried out at a temperature of from room temperature to 100° C. for 1 to 5 hours. After completion of the reaction, the reaction mixture is neutralized by an alkali, followed by extraction with ethyl acetate or the like to produce compound (VI). This compound (VI) is converted into compound (VII) in the same manner as in Process 1, followed by amination of compound (VII) in the same manner as in Process 1 to obtain compound (Ia).

Process 3

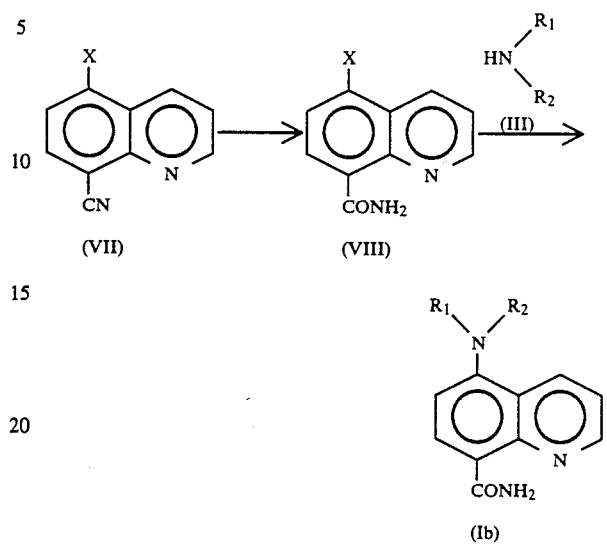

wherein X represents a halogen atom and $R_1$ and $R_2$ have the same meanings as defined above.

5-Halogeno-8-quinolinecarbonitrile (VII) is hydrolyzed into 5-halogeno-8-quinolinecarboxamide (VIII), which is reacted with an amino compound (III) to produce the quinoline derivative (Ib). The hydrolysis is implemented according to a conventional method, e.g. by dissolving compound (VII) into a solvent and stirring the mixture in the presence of a base and 30% hydrogen peroxide at a temperature of from room temperature to 50° C. It is desirable to use an alcohol such as methanol, ethanol, or the like is used as a solvent and an inorganic base such as sodium hydroxide, potassium hydroxide, or the like as a base. Amination is effected to 5-halogeno-8-quinolinecarboxamide (VIII) thus obtained in the same manner as Process 1 to produce compound (Ib).

Process 4

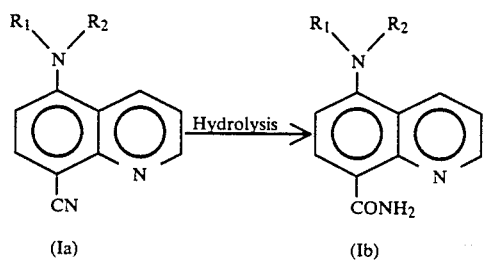

wherein $R_1$ and $R_2$ have the same meanings as defined above. 5-substituted-8-quinolinecarboxamide (Ib) can be produced by the hydrolysis of 5-substituted-8-quinolinecarbonitrile (Ia). The reaction is carried out exactly in the same manner as the hydrolysis reaction of Process 3.

Process 5

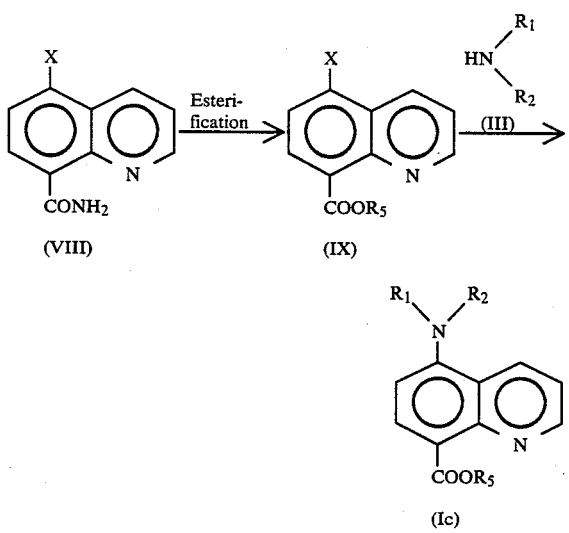

wherein X represents a halogen atom, $R_5$ represents a lower alkyl group, and $R_1$ and $R_2$ have the same meanings as defined above.

5-Halogeno-8-quinolinecarboxamide (VIII) is esterified into 5-halogeno-8-quinolinecarboxylic acid ester (IX). The quinoline derivative (Ic) is produced by the reaction of compound (IX) and an amino compound (III). The esterification of compound (VIII) is implemented according to a known method, e.g. by stirring the mixture of compound (VIII) and an anhydrous alcohol in the presence of an acid catalyst at a temperature from room temperature to the refluxing point of the alcohol used for several hours. Use of a strong acid such as hydrochloric acid or sulfuric acid is desirable. 5-Halogeno-8-quinolinecarboxylic acid ester (IX) thus obtained is reacted with an amino compound (III) according to the same manner as in Process 1 to produce compound (Ic).

Process 6

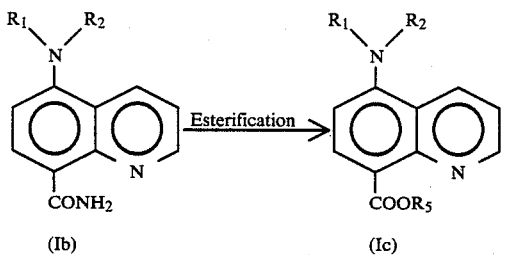

wherein $R_1$ and $R_2$ have the same meanings as defined previously.

5-Substituted-8-quinolinecarboxylic acid ester (Ic) is produced by the esterification of 5-substituted-8-quinolinecarboxamide (Ib).

The reaction is performed in the same manner as in the reaction of Process 5.

The quinoline derivative (I) produced in either of the processes illustrated above can be converted by a conventional method, as required, into an inorganic salt such as hydrochloride, hydrobromide, nitrate, sulfate, or the like, or into an organic salt such as acetate, citrate, maleate, fumalate, lactate, methane sulfonate, or the like.

Pharmaceutical actions of the compounds of this invention were tested.

(1) Cardiotonic Activity

Hearts of Hartley guinea pigs (male, weight: 400–600 g) were taken out of mus'culi papilla'ris ventric'uri dex'tri was enucleated from each heart in Krebs-bicarbonate solution. This test specimen was suspended in a 20 ml bath containing Krebs-bicarbonate solution at 32° C. aerated with a 95% $O_2$ and 5% $CO_2$ mixed gas with its mus'curi papilla'res base being fixed at a static tension of 0.5 g. A transparietal electroversion (voltage: twice of the threshold voltage; 0.5 Hz, 3 msec.) was applied to measure the contraction force.

After stabilizing the test specimen, a test compound dissolved into 1N hydrochloric acid and diluted to $10^{-5}$ g/ml with physiological saline was administered. Maximum rate of the change ($\Delta\%$) in contraction force after administration vs. before administration of the test compound was taken as a standard for the cariotonic activity (contraction increase effect) of the compound. The results are shown in Table 1, in which compound numbers designate those shown in Table 3.

TABLE 1

| Compound No. | Contraction Increase (%) |
|---|---|
| 2 | 36.7 |
| 4 | 38.8 |
| 7 | 46.4 |
| 13 | 39.5 |
| 20 | 35.0 |
| 21 | 28.5 |
| 22 | 35.0 |

(2) Vasodilative Activity

A bastard, male, adult dog weighing about 10 kg was respirated under narcosis. Its right arteria femola'lis was exposed with administration of heparin. An artificial circuit containing on an electro-magnetic blood flowmeter probe was established to measure the blood flow through the right arteria femola'lis.

The change (%) in blood flow before and after administration of the test compound to the circuit in an amount of 1 to 300 μg (the maximum dose that does not affect the general blood pressure) was calculated. The value was taken as an $ED_{100}$ (A). As a control, the corresponding $ED_{100}$ value (B) for papaverine.HCl in an amount of 1 to 300 μg (the maximum dose that does not affect the general blood pressure) was determined for comparison. Vasodilative activities of the compounds were determined as the ratio B/A. The results are shown in Table 2, in which compound numbers designate those shown in Table 3.

TABLE 2

| Compound No. | Vasodilative Activity |
|---|---|
| 15 | 0.86 |
| 21 | 0.36 |
| 35 | 0.56 |
| 44 | 3.70 |
| papaverine.HCl | 1.00 |

As demonstrated by the above experiment the compound of this invention exhibits superior cardiotonic activity and vasodilative activity, and thus is effective as a medicine.

Other features of the invention will become apparent in the course of the following description of the exemplary embodiments which are given for illustration of the invention and are not intended to be limiting thereof.

EXAMPLES

EXAMPLE 1

5-Morpholino-8-nitroquinoline, 3.90 g, was dissolved into 30 ml of water and 30 ml of hydrochloric acid. To this mixture 10.2 g of stannous chloride.dihydrate was added and the mixture was heated on a water bath under stirring for 1 hour. After cooling, the mixture was neutralized with potassium carbonate and extracted with ethyl acetate. The extract was dried over anhydrous sodium sulfate. Ethyl acetate was evaporated to produce 1.83 g (yield: 53%) of 8-amino-5-morpholinoquinoline. This compound was dissolved into 10 ml of water and 6 ml of concentrated HCl, and to the solution an aqueous solution containing 0.62 g of sodium nitrite was added dropwise while stirring at $-15°$ C. The diazonium salt thus obtained was neutralized with sodium bicarbonate, and resulting product was added at 0° C. into an aqueous solution of cuprous cyanide (prepared from 2.0 g of cuprous chloride and 3.4 g of potassium cyanide). The mixture was stirred at the same temperature for 1 hour, then at 70° C. for 30 minutes to complete the reaction. The reaction mixture was extracted with ethyl acetate and the extract was dried over anhydrous sodium sulfate. Ethyl acetate was evaporated and the residue was refined by column chromatography on silica gel using a chloroform-n-hexane (3:2) mixed solvent as an eluent. The crystals thus obtained were recrystallized from ethanol to yield 0.12 g (yield: 6.2%) of 5-morpholino-8-quinolinecarbonitrile (Compound No. 13)

EXAMPLE 2

5-Chloro-8-nitroquinoline, 5 g, was reduced, diazonized, and cyanized in the same manner as in Example 1 to produce 2.62 g (yield: 58%) of 5-chloro-8-quinolinecarbonitrile. A mixture of 1.88 g of 5-chloro-8-quinolinecarbonitrile thus prepared and 7.10 g of pyrrolidine was dissolved into 30 ml of 2-ethoxyethanol and the solution was heated under reflux for 3 hours. The solvent was evaporated, and the residue, after addition of water, was extracted with chloroform. The extract was washed with water and dried over anhydrous sodium sulfate. Chloroform was evaporated, and the residue was refined by column chromatography on silica gel using a chloroform-methanol (95:5) mixed solvent as an eluent. The crystals thus obtained were recrystallized from ethanol to yield 1.54 g (yield: 69%) of 5-pyrrolidino-8-quinolinecarbonitrile (Compound No. 7).

EXAMPLE 3

5-Chloro-8-quinolinecarbonitrile, 0.50 g, and imidazole, 1.80 g, were dissolved into 30 ml of pyridine. To the solution 0.36 g of anhydrous potassium carbonate was added and the mixture was heated under reflux for 8 hours. After separating indissolved substance by filtration, the solvent was evaporated and the residue was refined by column chromatography on silica gel using chloroform as an eluent. The crystals obtained were recrystallized from ethanol to yield 0.35 g (yield: 60%) of 5-imidazolyl-8-quinolinecarbonitrile (Compound No. 20).

EXAMPLE 4

To 0.8 g of 5-morpholino-8-quinolinecarbonitrile (Compound No. 13) 60 ml of methanol was added and the mixture was stirred at 0° C. with further addition of an aqueous solution of 0.47 g of potassium hydroxide and then 5 ml of 30% hydrogen peroxide aqueous solution. The mixture was heated at 40° to 50° C. for 16 hours with stirring. After evaporation of the solvent, saturated sodium chloride aqueous solution was added to the residue, which was extracted with chloroform, and the extract was dried over anhydrous sodium sulfate. Chloroform was evaporated, and the residue was refined by column chromatography on silica gel using chloroform as an eluent. The crystals thus obtained were recrystallized from ethanol to yield 0.48 g (yield: 56%) of 5-morpholino-8-quinolinecarboxamide (Compound No. 22).

EXAMPLE 5

To 0.17 g of 5-morpholino-8-quinolinecarboxamide (Compound No. 22) 10 ml of anhydrous ethanol and 2 ml of concentrated sulfuric acid were added, and the mixture was heated under reflux. The solvent was evaporated and the residue was neutralized with saturated aqueous solution of sodium bicarbonate. After extraction with ethyl acetate, the extract was washed with saturated aqueous solution of sodium chloride, and dried over anhydrous sodium sulfate. Ethyl acetate was evaporated, and the residue was refined by column chromatography on silica gel using chloroform-n-hexane (3:2) as an eluent. The crystals thus obtained were recrystallized from chloroform-ether to yield 0.16 g (yield: 85%) of ethyl 5-morpholino-8-quinolincarboxylate (Compound No. 23).

EXAMPLE 6

Compounds listed in Table 3 were prepared according to the same manner as Examples 1 to 5. Table 3 also lists the compounds prepared in Examples 1 to 5.

TABLE 3

| Compd. No. | $R_1\diagdown N\diagup R_2$ | $R_3$ | Melting Point (°C.) | NMR δ (ppm in CDCl$_3$*; in CD$_3$OD**; DMSO-d$_6$) |
|---|---|---|---|---|
| 1 | —NHCH$_2$CH$_2$OH | CN | 199–200 | 3.51 (t, 2H), 3.87 (t, 2H), 6.65 (d, 1H), 7.48 (dd, 1H), 7.95 (d, 1H), 8.61 (dd, 1H), 8.88 (dd,1H).* |
| 2 | —NHCH$_2$CH$_2$CH$_2$OH | CN | 202.5–203 | 1.73–2.26 (m, 2H), 3.26–4.00 (m, 4H), 6.56 (d, 1H), 7.43 (dd, 1H), 7.89 (d, 1H), 8.45 (dd, 1H), 8.86 (dd, 1H).* |
| 3 | —NHCH$_2$CH$_2$OAc | CN | 204–206 | 2.00 (s, 3H), 3.34 (s, 1H), 3.40–3.80 (m, 2H), 4.28 (t, 2H), 6.70 (d, 1H), 7.55 (dd, 1H), 8.00 (d, 1H), 8.78 (dd, 1H), 8.98 (dd, 1H). |
| 4 | —NHCH$_2$CH$_2$CH$_2$OAc | CN | 149.5–150.5 | 1.67–2.33 (m, 5H), 3.26–3.66 (m, 2H), 4.26 (t, 2H), 5.60 (br, 1H), 6.55 (d, 1H), 7.40 (dd, 1H), 7.89 (d, 1H), 8.26 (dd, 1H), 8.97 (dd, 1H). |
| 5 | —N(CH$_2$CH$_2$OH)$_2$ | CN | 140–141 | 3.40–3.60 (m, 4H), 3.70–4.00 (m, 4H), 6.70 (d, 1H), 7.50 (dd, 1H), 7.94 (d, 1H), 8.60 (dd, 1H), 8.88 (dd, 1H).* |
| 6 | —NHCH$_2$CH$_2$N(CH$_3$)$_2$ | CN | 125–127 | 2.31 (s, 6H), 2.70 (t, 2H), 3.18–3.40 (m, 2H), 6.02 (br, 1H), 6.49 (d, 1H), 7.41 (dd, 1H), 7.91 (d, 1H), 8.20 (dd, 1H), 9.00 (dd, 1H) |
| 7 | 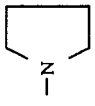 | CN | 176–178 | 1.75–2.30 (m, 4H), 3.20–3.80 (m, 4H), 6.55 (d, 1H), 7.30 (dd, 1H), 7.80 (d, 1H), 8.55 (dd, 1H), 8.90 (dd, 1H). |
| 8 | 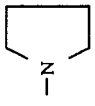 | CN | 155–155.5 | 1.50–2.40 (m, 5H), 3.20–4.30 (m, 5H), 6.90 (d, 1H), 7.35 (dd, 1H), 7.88 (d, 1H), 8.50 (dd, 1H), 8.90 (dd, 1H). |
| 9 | 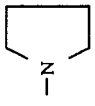 | CN | — Oily substance | 1.89 (s, 3H), 1.67–2.66 (m, 4H), 3.17–4.50 (m, 5H), 7.04 (d, 1H), 7.40 (dd, 1H), 7.90 (d, 1H), 8.50 (dd, 1H), 9.00 (dd, 1H). |
| 10 | 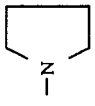 | CN | 112–113.5 | 1.50–2.00 (m, 6H), 3.00–3.30 (m, 4H), 7.05 (d, 1H), 7.50 (dd, 1H), 8.05 (d, 1H), 8.45 (dd, 1H), 9.05 (dd, 1H). |
| 11 | 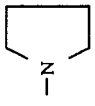 | CN | 184–185 | 1.50–2.50 (m, 5H), 2.66–3.69 (m, 4H), 4.00 (br, 1H), 7.00 (d, 1H), 7.40 (dd, 1H), 7.90 (dd, 1H), 8.40 (dd, 1H), 8.92 (dd, 1H). |

TABLE 3-continued

| Compd. No. | $\overset{R_1}{\underset{R_2}{\diagdown}}N-$ | $R_3$ | Melting Point (°C.) | NMR δ(ppm in CDCl₃*; in CD₃OD**; DMSO-d₆) |
|---|---|---|---|---|
| 12 | −N⟨⟩−OAc (piperidine with OAc) | CN | 147–148.5 | 1.56–2.40 (m, 7H), 2.83–3.66 (m, 4H), 4.83–5.30 (m, 1H), 7.06 (d, 1H), 7.50 (dd, 1H), 8.03 (d, 1H), 8.40 (dd, 1H), 9.00 (dd, 1H) |
| 13 | −N⟨⟩O (morpholine) | CN | 180–181 | 3.05–3.40 (m, 4H), 3.80–4.50 (m, 4H), 7.10 (d, 1H), 7.50 (dd, 1H), 8.10 (d, 1H), 8.50 (dd, 1H), 9.00 (dd, 1H). |
| 14 | −N⟨⟩NH (piperazine) | CN | 132–134 | 3.20 (s, 8H), 7.15 (d, 1H), 7.55 (dd, 1H), 8.10 (d, 1H), 8.50 (dd, 1H), 9.05 (dd, 1H). |
| 15 | −N⟨⟩N−CH₃ | CN | 159–160 | 2.43 (s, 3H), 2.50–3.00 (m, 4H), 3.00–3.40 (m, 4H), 7.06 (d, 1H), 7.45 (dd, 1H), 7.95 (d, 1H), 8.45 (d, 1H), 9.00 (dd, 1H) |
| 16 | −N⟨⟩N−CH₂CH₂OH | CN | 150–151 | 2.60–2.90 (m, 6H), 3.10–3.30 (m, 4H), 3.50–3.90 (t, 2H), 7.10 (d, 1H), 7.50 (dd, 1H), 8.05 (d, 1H), 8.50 (dd, 1H), 9.05 (dd, 1H). |
| 17 | −N⟨⟩N−CHO | CN | 189–191 | 3.00–3.40 (m, 4H), 3.50–4.00 (m, 4H), 7.10 (d, 1H), 7.55 (dd, 1H), 8.05 (d, 1H), 8.20 (s, 1H), 8.50 (dd, 1H), 9.05 (dd, 1H). |
| 18 | −N⟨⟩N−COCH₃ | CN | 188–190 | 2.20 (s, 3H), 3.00–3.40 (m, 4H), 3.60–4.10 (m, 4H), 7.05 (d, 1H), 7.55 (dd, 1H), 8.05 (d, 1H), 8.50 (dd, 1H), 9.00 (dd, 1H). |
| 19 | −N⟨⟩N−COCH(CH₃)₂ | CN | 172–173 | 1.09 (s, 3H), 1.23 (s, 3H), 2.63–3.00 (m, 5H), 3.66–4.07 (m, 4H), 7.03 (d, 1H), 7.50 (dd, 1H), 8.00 (d, 1H), 8.43 (dd, 1H), 9.00 (dd, 1H). |

TABLE 3-continued

| Compd. No. | R1\N\R2 | R3 | Melting Point (°C.) | NMR δ(ppm in CDCl3*; in CD3OD**; DMSO-d6) |
|---|---|---|---|---|
| 20 | [imidazol-1-yl: -N\<CH=N/CH=CH] | CN | 210-212 | 7.23-7.50 (m, 2H), 7.50-7.95 (m, 3H), 8.00-8.40 (m, 2H), 9.15 (dd, 1H). |
| 21 | [pyrrolidin-1-yl] | CONH2 | 229-231 | 1.72 (s, 2H), 1.72-2.10 (m, 4H), 3.35-3.80 (m, 4H), 6.84 (d, 1H), 7.28 (dd, 1H), 8.64 (dd, 1H), 8.68 (d, 1H), 8.80 (dd, 1H). |
| 22 | [morpholin-4-yl] | CONH2 | 243-245 | 3.00-3.30 (m, 4H), 3.80-4.10 (m, 4H), 6.10 (br, 2H), 7.20 (d, 1H), 7.45 (dd, 1H), 8.60 (dd, 1H), 8.80 (d, 1H), 8.90 (dd, 1H). |
| 23 | [morpholin-4-yl] | CO2Et | 103-105 (Hydrochloride) | 1.40 (t, 3H), 2.90-3.30 (m, 4H), 3.80-4.20 (m, 4H), 4.50 (q, 2H), 7.05 (d, 1H), 7.40 (dd, 1H), 8.00 (d, 1H), 8.45 (dd, 1H), 9.00 (dd, 1H). |
| 24 | —NHCH3 | CN | 221.5-222.5 | 3.05 (d, 3H), 5.20 (br, 1H), 6.55 (dd, 1H), 7.45 (dd, 1H), 8.00 (d, 1H), 8.15 (dd, 1H), 9.04 (dd, 1H). |
| 25 | —NH—C4H9-n | CN | 199.5-200 | 1.00 (t, 3H), 1.20-2.00 (m, 4H), 3.20-3.45 (m, 2H), 5.05 (br, 1H), 6.55 (d, 1H), 7.44 (dd, 1H), 7.96 (d, 1H), 8.20 (dd, 1H), 9.05 (dd, 1H). |
| 26 | —NHCH(CH3)CH2OH | CN | 212-214 | 1.35 (d, 3H), 3.60-4.00 (m, 4H), 6.59 (d, 1H), 7.50 (dd, 1H), 8.00 (d, 1H), 8.55 (dd, 1H), 9.00 (dd, 1H).* |
| 27 | —NHCH2CH(OH)CH2OH | CN | 188-190.5 | 3.40-3.80 (m, 4H), 3.90-4.15 (m, 1H), 6.71 (d, 1H), 7.55 (dd, 1H), 8.00 (d, 1H), 8.70 (dd, 1H), 8.96 (dd, 1H).* |
| 28 | —NH(CH2)4OH | CN | 176-178 | 1.40-2.00 (m, 4H), 3.20-3.44 (m, 2H), 3.65 (t, 2H), 6.50 (d, 1H), 7.50 (dd, 1H), 7.90 (d, 1H), 8.50 (dd, 1H), 8.90 (dd, 1H).* |
| 29 | —NH(CH2)6OH | CN | 134.5-135.5 | 1.00-2.00 (m, 8H), 3.20-3.50 (m, 2H), 3.50-3.80 (m, 2H), 6.53 (d, 1H), 7.40 (dd, 1H), 7.90 (d, 1H), 8.24 (dd, 1H), 8.24 (dd, 1H), 9.00 (dd, 1H).* |
| 30 | —NH(CH2)3NH2 | CN | 154-156 | 2.00 (q, 2H), 2.95 (t, 2H), 3.45 (t, 2H), 6.59 (d, 1H), 7.50 (dd, 1H), 7.98 (d, 1H), 8.60 (dd, 1H), 9.00 (dd, 1H).* |
| 31 | —NHCH2CHCH2NH2<br>     \|<br>     OH | CN | 188.5-200 | 2.60-2.75 (m, 2H), 2.80-3.90 (m, 6H), 6.65 (d, 1H), 7.40-7.80 (dd, br, 2H), 7.90 (d, 1H), 8.75 (dd, 1H), 8.95 (dd, 1H).** |
| 32 | —NHCH2CH(OH)Ph | CN | 215-216 | 3.45-3.64 (dd, 2H), 5.00-5.20 (dd, 1H), 6.65 (d, 1H), 7.40-7.65 (m, 6H), 7.96 (d, 1H), 8.50 (dd, 1H), 9.02 (dd, 1H).* |
| 33 | —NHCH2Ph | CN | 178-179 | 4.55 (d, 2H), 5.50 (t, 1H), 7.24-7.50 (m, 6H), 6.55 (d, 1H), 7.90 (d, 1H), 8.24 (dd, 1H), 9.00 (dd, 1H). |
| 34 | —NH(CH2)3NHCON(CH3)2 | CN | 200-202 | 1.70-2.10 (m, 2H), 2.20 (s, 6H), 2.92 (s, 6H), 3.20-3.55 (m, 5H), 6.50 (d, 1H), 7.45 (dd, 1H), 7.90 (d, 1H), 8.60 (dd, 1H), 8.96 (dd, 1H).* |

TABLE 3-continued
| Compd. No. | R1\N\R2 | R3 | Melting Point (°C.) | NMR δ(ppm in CDCl3*; in CD3OD**; DMSO-d6) |
|---|---|---|---|---|
| 35 | —N(CH3)2 | CN | 112–114 | 3.03 (s, 6H), 6.95 (d, 1H), 7.45 (dd, 1H), 7.95 (d, 1H), 8.50 (dd, 1H), 9.00 (dd, 1H). |
| 36 | 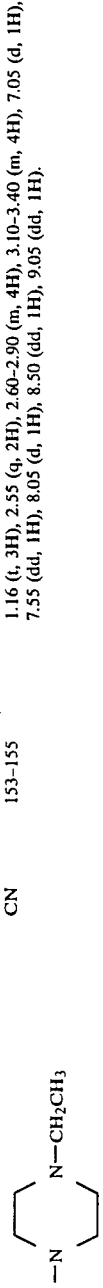 | CN | 153–155 | 1.16 (t, 3H), 2.55 (q, 2H), 2.60–2.90 (m, 4H), 3.10–3.40 (m, 4H), 7.05 (d, 1H), 7.55 (dd, 1H), 8.05 (d, 1H), 9.05 (dd, 1H). |
| 37 |  | CN | 145–146 | 0.65–1.85 (m, 7H), 2.30–3.00 (m, 6H), 3.00–3.40 (m, 4H), 7.10 (d, 1H), 7.50 (dd, 1H), 8.05 (d, 1H), 8.45 (dd, 1H), 9.03 (dd, 1H). |
| 38 |  | CN | 104–105.5 | 0.60–1.85 (m, 11H), 2.20–2.90 (m, 6H), 3.00–3.35 (m, 4H), 7.05 (dd, 1H), 7.45 (dd, 1H), 8.50 (dd, 1H), 9.03 (dd, 1H). |
| 39 | 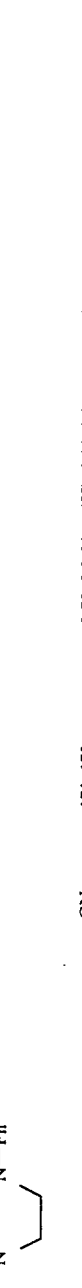 | CN | 231–233 | 3.10–3.60 (m, 8H), 6.80–7.30 (m, 6H), 7.50 (dd, 1H), 8.00 (d, 1H), 8.50 (dd, 1H), 9.00 (dd, 1H). |
| 40 |  | CN | 171–173 | 2.70–3.00 (m, 4H), 3.00–3.35 (m, 4H), 3.38 (s, 2H), 3.67 (s, 8H), 7.10 (d, 1H), 7.50 (dd, 1H), 8.05 (d, 1H), 8.45 (dd, 1H). |
| 41 | 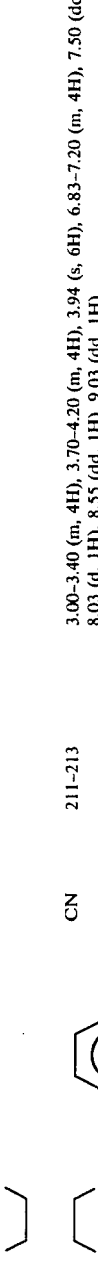 | CN | 214–216 | 2.92 (s, 6H), 3.05–3.35 (m, 4H), 3.35–3.73 (m, 4H), 7.10 (d, 1H), 7.50 (dd, 1H), 8.05 (d, 1H), 8.50 (dd, 1H), 9.03 (dd, 1H). |
| 42 |  | CN | 211–213 | 3.00–3.40 (m, 4H), 3.70–4.20 (m, 4H), 3.94 (s, 6H), 6.83–7.20 (m, 4H), 7.50 (dd, 1H), 8.03 (d, 1H), 8.55 (dd, 1H), 9.03 (dd, 1H). |

TABLE 3-continued

| Compd. No. | $\begin{array}{c}R_1\\ \diagdown N\diagup\\ R_2\end{array}$ | $R_3$ | Melting Point (°C.) | NMR δ(ppm in CDCl₃*: in CD₃OD**: DMSO-d₆) |
|---|---|---|---|---|
| 43 | N-piperidinyl-(2-chlorophenyl) | CN | 223–226 | 3.38 (s, 8H), 6.90–7.50 (m, 5H), 7.15 (d, 1H), 7.50 (dd, 1H), 8.05 (d, 1H), 8.55 (dd, 1H), 9.08 (dd, 1H). |
| 44 | N-methylpiperazinyl (N—CH₃) | CONH₂ | 198–200 | 2.43 (s, 3H), 2.50–2.80 (m, 4H), 3.00–3.30 (m, 4H), 6.10 (br, 1H), 7.20 (d, 1H), 7.45 (dd, 1H), 8.55 (dd, 1H), 8.75 (d, 1H), 8.90 (dd, 1H). |
| 45 | piperidinyl | CONH₂ | 179–181 | 1.45–2.15 (m, 6H), 2.95–3.25 (m, 4H), 6.10 (br, 2H), 7.15 (d, 1H), 7.45 (dd, 1H), 8.55 (dd, 1H), 8.75 (d, 1H), 8.90 (dd, 1H). |
| 46 | 4-hydroxypiperidinyl | CONH₂ | 226–228 | 1.60–2.30 (m, 4H), 2.65–3.10 (m, 2H), 3.20–3.50 (m, 2H), 3.70–4.00 (m, 1H), 7.25 (d, 1H), 7.55 (dd, 1H), 8.65 (ddd, 2H), 8.96 (dd, 1H).* |
| 47 | —NH(CH₂)₃OH | CONH₂ | 211–213 | 1.80–2.15 (m, 2H), 3.48 (t, 2H), 3.80 (t, 2H), 6.68 (d, 1H), 7.44 (dd, 1H), 8.50 (dd, 1H), 8.60 (d, 1H), 8.88 (dd, 1H).* |
| 48 | —NHCHCH₂OH <br>     \|<br>    CH₃ | CONH₂ | 204–205 | 1.35 (d, 3H), 3.68–4.08 (m, 3H), 6.70 (d, 1H), 7.42 (dd, 1H), 8.56 (ddd, 2H), 8.88 (dd, 1H).* |
| 49 | —NHCH₂CHCH₂OH <br>         \|<br>       OH | CONH₂ | 219–222 | 3.50 (d, 2H), 3.70 (d, 2H), 3.84–4.20 (m, 1H), 6.71 (d, 1H), 7.45 (dd, 1H), 8.55 (dd, 1H), 8.60 (d, 1H), 8.92 (dd, 1H).* |
| 50 | —NHCH₃ | CONH₂ | 250–252 | 3.04 (d, 3H), 6.60 (d, 1H), 7.44 (dd, 1H), 8.48 (dd, 1H), 8.62 (d, 1H), 8.88 (dd, 1H).* |
| 51 | —N(CH₃)₂ | CONH₂ | 185.5–186.5 | 2.93 (s, 6H), 7.10 (d, 1H), 7.42 (dd, 1H), 8.56 (dd, 1H), 8.76 (d, 1H), 8.88 (dd, 1H). |
| 52 | N-formylpiperazinyl (N—CHO) | CONH₂ | 230–231.5 | 2.75–3.30 (m, 6H), 3.55–4.00 (m, 4H), 7.24 (d, 1H), 7.56 (dd, 1H), 8.14 (s, 1H), 8.64 (dd, 1H), 8.76 (d, 1H), 8.98 (dd, 1H). |

TABLE 3-continued

| Compd. No. | R1\N/R2 | R3 | Melting Point (°C.) | NMR δ(ppm in CDCl3*; in CD3OD**; DMSO-d6) |
|---|---|---|---|---|
| 53 | 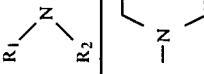 | COOEt | Oily substance | 1.43 (t, 3H), 2.43 (s, 3H), 2.56–2.84 (m, 4H), 3.04–3.30 (m, 4H), 4.48 (q, 2H), 7.09 (d, 1H), 7.40 (dd, 1H), 8.04 (d, 1H), 8.50 (dd, 1H), 9.04 (dd, 1H). |
| 54 | 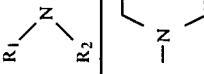 | COOEt | Oily substance | 1.42 (t, 3H), 1.70–2.10 (m, 4H), 3.20–3.40 (m, 4H), 4.44 (q, 2H), 6.72 (d, 7.28 (dd, 1H), 8.05 (d, 1H), 8.52 (dd, 1H), 9.00 (dd, 1H). |
| 55 | —NH(CH2)3—N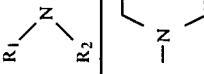 | CN | 158–159.5 | 1.75–2.15 (m, 2H), 2.40–2.80 (m, 6H), 3.24–3.52 (m, 2H), 3.60–4.00 (m, 4H), 6.41 (d, 1H), 7.40 (dd, 1H), 7.24–7.50 (br, 1H), 7.84 (d, 1H), 8.35 (dd, 1H), 9.00 (dd, 1H) |
| 56 | —N(CH3)2 | COOEt | Oily substance | 1.43 (t, 3H), 2.93 (s, 6H), 4.50 (q, 2H), 7.02 (d, 1H), 7.40 (dd, 1H), 8.02 (d, 1H), 8.52 (dd, 1H), 9.04 (dd, 1H). |
| 57 | 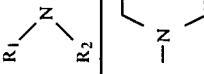 | COOEt | Oily substance | 1.43 (t, 3H), 1.60–2.30 (m, 4H), 2.70–3.08 (m, 2H), 3.16–3.50 (m, 2H), 3.76–4.12 (m, 1H), 4.50 (q, 2H), 7.06 (d, 1H), 7.44 (dd, 1H), 8.01 (d, 1H), 8.48 (dd, 1H), 9.04 (dd, 1H). |
| 58 | —NHCH2CH3 | CN | 220.5–222 | 1.43 (t, 3H), 3.40 (q, 2H), 6.56 (d, 1H), 7.44 (dd, 1H), 7.95 (d, 1H), 8.20 (dd, 1H), 9.04 (dd, 1H). |
| 59 | —NHCH2CH3 | CONH2 | 241–243 | 1.40 (t, 3H), 3.40 (q, 2H), 6.65 (d, 1H), 7.42 (dd, 1H), 8.53 (dd, 1H), 8.60 (d, 1H), 8.88 (dd, 1H).* |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A quinoline derivative represented by the following formula (I):

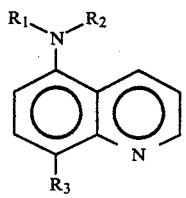

wherein $R_1$ represents hydrogen, alkyl, or substituted alkyl and $R_2$ represents alkyl or substituted alkyl, wherein the substituent groups on said alkyl groups of groups $R_1$ and $R_2$ are selected from the group consisting of hydroxyl, amino, alkylamino, dialkylamino, morpholino, aryl, ureido, ureido substituted by alkyl, or acyloxy; or $R_1$ and $R_2$ in combination with each other and with the adjacent nitrogen atom form a heterocyclic ring system selected from the group consisting of pyrrolidine, piperidine, piperazine, morpholine, pyrrole, imidazole, pyridine or pyrimidine, or said heterocyclic ring system substituted by (i) alkyl; (ii) alkyl substituted by hydroxyl, amino, alkylamino, dialkylamino, morpholino, aryl, ureido, ureido substituted by alkyl, acyloxy, or

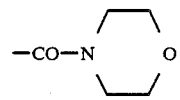

or (iii) a substituent selected from the group consisting of hydroxyl, amino, alkylamino, dialkylamino, morpholino, aryl, ureido, ureido substituted by alkyl, acyloxy, formyl, carbamoyl, carbamoyl substituted by alkyl, or acyl; and $R_3$ is cyano, carbamoyl or alkoxycarbonyl.

2. A quinoline according to claim 1, which is 5-morpholino-8-quinolinecarbonitrile.

3. A quinoline according to claim, 1 which is 5-pyrrolidino-8-quinolinecarbonitrile.

4. A quinoline according to claim 1, which is 5-imidazolyl-8-quinolinecarbonitrile.

5. A quinoline according to claim 1, which is 5-morpholino-8-quinolinecarboxamide.

6. A quinoline according to claim 1, which is ethyl-5-morpholino-8-quinolinecarboxylate.

* * * * *

UNITED STATES PATENT AND TRADEMARK OFFICE
CERTIFICATE OF CORRECTION

PATENT NO. : 4,933,447
DATED : June 12, 1990
INVENTOR(S) : Fujiko KONNO, et al

It is certified that error appears in the above-identified patent and that said Letters Patent is hereby corrected as shown below:

On the title page, under items [19] and [75]:

The first inventor's last name has been misspelled, it should read:

--Konno--.

Signed and Sealed this

Third Day of September, 1991

Attest:

HARRY F. MANBECK, JR.

*Attesting Officer*  Commissioner of Patents and Trademarks